US00PP27605P2

(12) United States Plant Patent
Ochiai

(10) Patent No.: US PP27,605 P2
(45) Date of Patent: Jan. 24, 2017

(54) ***PERICALLIS* PLANT NAMED 'OCHKEIBU'**

(50) Latin Name: *Pericallis cruenta*
Varietal Denomination: Ochkeibu

(71) Applicant: Shigeaki Ochiai, Gose (JP)

(72) Inventor: Shigeaki Ochiai, Gose (JP)

( * ) Notice: Subject to any disclaimer, the term of this patent is extended or adjusted under 35 U.S.C. 154(b) by 0 days.

(21) Appl. No.: 14/756,529

(22) Filed: Sep. 15, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

PLUTO Plant Variety Database Aug. 10, 2016 p. 1.*

* cited by examiner

*Primary Examiner* — Annette Para
(74) *Attorney, Agent, or Firm* — C. A. Whealy

(57) ABSTRACT

A new and distinct cultivar of *Pericallis* plant named 'Ochkeibu', characterized by its compact, upright and mounded plant habit; freely branching growth habit; freely flowering habit; and daisy-type inflorescences with violet blue-colored ray florets that are lighter in color towards the center of the inflorescence.

1 Drawing Sheet

Botanical designation: *Pericallis cruenta.*
Cultivar denomination: 'OCHKEIBU'.

CROSS REFERENCED TO CLOSELY-RELATED APPLICATIONS

Title: *Pericallis* Plant Named 'Ochkeinibu'
Applicant: Shigeaki Ochiai
Filed: Concurrently with this application

BACKGROUND OF THE INVENTION

The present invention relates to a new and distinct cultivar of *Pericallis* plant, botanically known as *Pericallis cruenta* and hereinafter referred to by the name 'Ochkeibu'.

The new *Pericallis* plant is a product of a planned breeding program conducted by the Inventor in Gose City, Nara, Japan. The objective of the breeding program is to create new compact *Pericallis* plants with numerous attractive flowers.

The new *Pericallis* plant originated from an open-pollination made by the Inventor during the spring of 2008 in Gose City, Nara, Japan of a proprietary selection of *Pericallis cruenta* identified as code number FC20-3-005, not patented, as the female, or seed, parent with an unknown selection of *Pericallis cruenta* as the male, or pollen, parent. The new *Pericallis* plant was discovered and selected by the Inventor as a single flowering plant from within the progeny of the stated open-pollination in a controlled greenhouse environment in Gose City, Nara, Japan during the spring of 2009.

Asexual reproduction of the new *Pericallis* plant by vegetative terminal cuttings in a controlled greenhouse environment in Gose City, Nara, Japan since the spring of 2009 has shown that the unique features of this new *Pericallis* plant are stable and reproduced true to type in successive generations.

SUMMARY OF THE INVENTION

Plants of the new *Pericallis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Ochkeibu'. These characteristics in combination distinguish 'Ochkeibu' as a new and distinct *Pericallis* plant:

1. Compact, upright and mounded plant habit.
2. Freely branching growth habit.
3. Freely flowering habit.
4. Daisy-type inflorescences with violet blue-colored ray florets that are lighter in color towards the center of the inflorescence.

Plants of the new *Pericallis* differ from plants of the female parent selection primarily in plant habit as plants of the new *Pericallis* are more compact than plants of the female parent selection.

Plants of the new *Pericallis* can be compared to plants of *Pericallis cruenta* 'Ochkeinibu', disclosed in a U.S. Plant Patent application filed concurrently. Plants of the new *Pericallis* and 'Ochkeinibu' differ primarily in ray floret color as plants of 'Ochkeinibu' have darker violet blue-colored ray florets.

Plants of the new *Pericallis* can also be compared to plants of *Senecio cruentus*×*Pericallis heritieri* 'Sunsenebu', disclosed in U.S. Plant Pat. No. 12,104. In side-by-side comparisons conducted in Gose City, Nara, Japan, plants of the new *Pericallis* differed from plants of 'Sunsenebu' in the following characteristics:

1. Plants of the new *Pericallis* were more compact than plants of 'Sunsenebu'.

2. Plants of the new *Pericallis* were more freely branching, had shorter internodes and were denser than plants of 'Sunsenebu'.
3. Plants of the new *Pericallis* had smaller and darker green-colored leaves than plants of 'Sunsenebu'.
4. Plants of the new *Pericallis* and 'Sunsenebu' differed in ray floret color as plants of 'Sunsenebu' had solid violet blue-colored ray florets.

BRIEF DESCRIPTION OF THE PHOTOGRAPH

The accompanying photograph illustrates the overall appearance of the new *Pericallis* plant showing the colors as true as it is reasonably possible to obtain in colored reproductions of this type. Colors in the photograph may differ slightly from the color values cited in the detailed botanical description which accurately describe the colors of the new *Pericallis* plant.

The photograph is a side perspective view of a typical flowering plant of 'Ochkeibu' grown in a container.

DETAILED BOTANICAL DESCRIPTION

The aforementioned photograph, following observations and measurements describe plants grown during the summer in 12-cm containers in a glass-covered greenhouse in Rheinberg, Germany and under cultural practices typically used in commercial *Pericallis* production. During the production of the plants, day and night temperatures averaged 18° C. and light levels averaged 4,500 lux. Measurements and numerical values represent averages for typical flowering plants. Plants were pinched one time and were 20 weeks old when the photograph and description were taken. In the following description, color references are made to The Royal Horticultural Society Colour Chart, 2001 Edition, except where general terms of ordinary dictionary significance are used.

Botanical classification: *Pericallis cruenta* 'Ochkeibu'.

Parentage:

*Female, or seed, parent*.—Proprietary selection of *Pericallis cruenta* identified as code number FC20-3-005, not patented.

*Male, or pollen, parent*.—Unknown selection of *Pericallis cruenta*, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Compact, upright and mounded plant habit; daisy-type inflorescences positioned above the foliar plane; freely branching habit with about ten to twelve lateral branches developing per plant; dense and bushy appearance; moderately vigorous growth habit.

*Plant height*.—About 20 cm.

*Plant diameter*.—About 20 cm.

*Lateral branches*.—Length: About 14 cm. Diameter: About 3.5 mm. Internode length: About 2.5 cm. Strength: Strong. Aspect: Upright to outwardly. Texture: Moderately pubescent. Luster: Matte. Color: Close to 146B.

*Leaf description*.—Arrangement: Alternate, simple. Length: About 4.2 cm. Width: About 5.3 cm. Shape: Reniform. Apex: Acute. Base: Cordate. Margin: Palmately lobed; crenate to serrate. Texture, upper and lower surfaces: Sparsely pubescent. Luster, upper and lower surfaces: Matte. Venation pattern: Pinnate; reticulate. Color: Developing leaves, upper surface: Close to N137B. Developing leaves, lower surface: Close to 137B. Fully expanded leaves, upper surface: Close to N137A; venation, close to N144C. Fully expanded leaves, lower surface: Close to 137B; venation, close to N144D. Petioles: Length: About 5.3 cm. Diameter: About 2 mm. Texture, upper and lower surfaces: Smooth, glabrous. Color, upper surface: Close to 144C tinted with close to N88B. Color, lower surface: Close to 144C.

Inflorescence description:

*Appearance*.—Daisy-type inflorescences with lanceolate-shaped ray florets; inflorescences arising from upper leaf axils and positioned above the foliar plane; disc and ray florets developing acropetally on a capitulum; inflorescences face mostly upright; freely flowering habit with about 87 inflorescences developing per plant during the flowering season.

*Fragrance*.—Faintly fragrant, pleasant.

*Natural flowering season*.—In Japan, plants of the new *Pericallis* flower continuously during the spring; plants begin flowering about six weeks after planting.

*Inflorescence longevity*.—Inflorescences last about two weeks on the plant; inflorescences not persistent.

*Inflorescence buds*.—Height: About 5.5 mm. Diameter: About 4.2 mm. Shape: Ovoid. Color: Close to 144A to 144B.

*Inflorescence size*.—Diameter: About 3.8 cm. Depth (height): About 8.5 mm. Disc diameter: About 1.1 cm.

*Receptacles*.—Height: About 6 mm. Diameter: About 1.1 cm. Color: Close to 144A.

*Ray florets*.—Length: About 2 cm. Width: About 6.1 mm. Shape: Lanceolate. Apex: Emarginate. Base: Obtuse. Margin: Entire. Texture, upper and lower surfaces: Smooth, glabrous. Luster, upper and lower surfaces: Matte. Number of ray florets per inflorescence: About 14 arranged in a single whorl. Color: When opening, upper surface: More blue than close to N89A. When opening, lower surface: Longitudinally striped, stripes, close to 91B and N89C. Fully opened, upper surface: Close to N89B; towards the base, close to N88C to N88D; color becoming closer to N89B to N89C with development. Fully opened, lower surface: Close to 92C to 92D; color becoming closer to 92D with development.

*Disc florets*.—Length: About 9 mm. Diameter: About 1 mm. Shape: Tubular; apex dentate, five-pointed.

Number of disc floret per inflorescence: About 87. Texture: Pubescent. Color, immature and mature: Apex: Close to N89A. Mid-section: Close to 145D. Base: Close to 145C.

*Phyllaries*.—Quantity per inflorescence: About 15 arranged in a single whorl. Length: About 1.3 cm. Width: About 3.3 mm. Shape: Ensiform. Apex: Acute. Base: Attenuate. Margin: Entire. Texture, upper surface: Smooth, glabrous. Texture, lower surface: Slightly pubescent. Color, upper surface: Close to 137A. Color, lower surface: Close to 137C.

*Peduncles*.—Length, terminal peduncle: About 3.2 cm. Length, fourth peduncle: About 5.5 cm. Length, seventh peduncle: About 9.2 cm. Diameter: About 2 mm. Strength: Strong. Aspect: Mostly upright. Texture: Smooth, glabrous. Color: Close to 144C.

*Reproductive organs*.—Androecium: Present on disc florets only. Filament length: About 0.5 mm. Filament color: Close to 144B. Anther length: About 1.5 mm. Anther shape: Narrowly elliptic. Anther color: Close to 83A. Pollen amount: Scarce to none. Pollen color: Close to 15A. Gynoecium: Present on both ray and disc florets. Pistil length: About 4 mm. Style length: About 1.5 mm. Style color: Close to 145D. Stigma shape: Decurrent. Stigma color: Close to 83A. Ovary color: Close to 149D.

*Seeds and fruits*.—Seed and fruit development has not been observed on plants of the new *Pericallis*.

Disease & pest resistance: Plants of the new *Pericallis* have not been observed to be resistant to pathogens and pests common to *Pericallis*.

Temperature tolerance: Plants of the new *Pericallis* have been observed to tolerate temperatures ranging from about 5° C. to about 40° C.

It is claimed:

1. A new and distinct *Pericallis* plant named 'Ochkeibu' as illustrated and described.

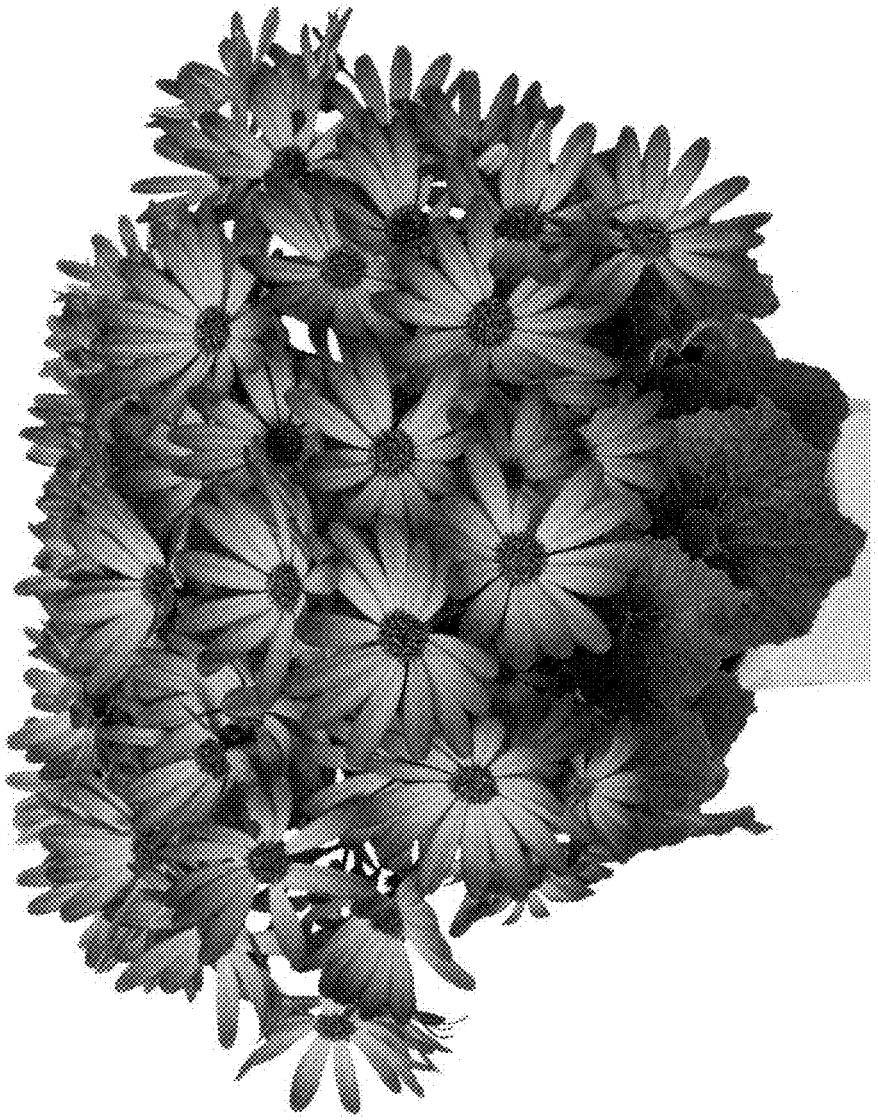

* * * * *